United States Patent [19]

Rajagopalan et al.

[11] Patent Number: 5,141,740
[45] Date of Patent: Aug. 25, 1992

[54] COMPLEXES AND COMPOSITIONS FOR MAGNETIC RESONANCE IMAGING AND USAGE METHODS

[75] Inventors: Raghavan Rajagopalan, Maryland Heights; Rebecca A. Wallace, Manchester; Muthunadar P. Periasamy, Creve Coeur, all of Mo.

[73] Assignee: Mallinckrodt Medical, Inc., St. Louis, Mo.

[21] Appl. No.: 616,450

[22] Filed: Nov. 21, 1990

[51] Int. Cl.$^5$ ............... G01N 24/00; G01N 31/00; A61K 31/28; C07F 5/00
[52] U.S. Cl. ........................ 424/9; 436/173; 436/806; 128/653.4; 514/492; 514/502; 514/836; 534/13; 534/16; 556/45; 556/57; 556/110; 556/138
[58] Field of Search ............... 424/9; 436/173, 806; 128/653 R, 653 CA, 654; 514/492, 502, 836; 534/13, 16; 556/45, 57, 110, 138

[56] References Cited

U.S. PATENT DOCUMENTS

| | | | |
|---|---|---|---|
| 4,647,447 | 3/1987 | Gries et al. | 424/9 |
| 4,687,658 | 8/1987 | Quay | 424/9 |
| 4,687,659 | 8/1987 | Quay | 424/9 |
| 4,826,673 | 5/1989 | Dean et al. | 424/9 |

OTHER PUBLICATIONS

Turowski, P. N. et al. Inorganic Chemistry 27(3):474–481 (1988).

Primary Examiner—Richard L. Raymond
Assistant Examiner—Gary E. Hollinden
Attorney, Agent, or Firm—Evan R. Witt

[57] ABSTRACT

Novel magnetic resonance imaging agents comprise complexes of paramagnetic ions with hydrazide derivatives of polyaminocarboxylic acid chelating agents. These novel imaging agents are characterized by excellent NMR image-contrasting properties and by high solubilities in physiological solutions. A novel method of performing an NMR diagnostic procedure involves administering to a warm-blooded animal an effective amount of a complex as described above and then exposing the warm-blooded animal to an NMR imaging procedure, thereby imaging at least a portion of the body of the warm-blooded animal.

34 Claims, No Drawings

COMPLEXES AND COMPOSITIONS FOR MAGNETIC RESONANCE IMAGING AND USAGE METHODS

BACKGROUND OF THE INVENTION

This invention relates to magnetic resonance imaging (MRI) and, more particularly, to methods and compositions for enhancing MRI.

The recently developed technique of magnetic resonance imaging encompasses the detection of certain atomic nuclei utilizing magnetic fields and radio-frequency radiation. It is similar in some respects to x-ray computed tomography (CT) in providing a cross-sectional display of the body organ anatomy with excellent resolution of soft tissue detail. As currently used, the images produced constitute a map of the proton density distribution and/or their relaxation times in organs and tissues. The technique of MR imaging is advantageously non-invasive as it avoids the use of ionizing radiation.

While the phenomenon of MRI was discovered in 1945, it is only relatively recently that it has found application as a means of mapping the internal structure of the body as a result of the original suggestion of Lauterbur (*Nature*, 242, 190–191 (1973)). The fundamental lack of any known hazard associated with the level of the magnetic and radio-frequency fields that are employed renders it possible to make repeated scans on vulnerable individuals. In addition to standard scan planes (axial, coronal, and sagittal), oblique scan planes can also be selected.

In an MRI experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin, when placed in an applied magnetic field (B, expressed generally in units of gauss or Tesla ($10^4$ gauss)) align in the direction of the field. In the case of protons, these nuclei precess at a frequency, f, of 42.6 MHz at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MR imaging, scanning planes and slice thicknesses can be selected. This selection permits high quality transverse, coronal and sagittal images to be obtained directly. The absence of any moving parts in MR imaging equipment promotes a high reliability. It is believed that MR imaging has a greater potential than CT for the selective examination of tissue characteristics in view of the fact that in CT, x-ray attenuation coefficients alone determine image contrast, whereas at least five separate variables ($T_1$, $T_2$, proton density, pulse sequence and flow) may contribute to the MR signal. For example, it has been shown (Damadian, *Science*, 171, 1151 (1971)) that the values of the $T_1$ and $T_2$ relaxation in tissues are generally longer by about a factor of 2 in excised specimens of neoplastic tissue compared with the host tissue.

By reason of its sensitivity to subtle physicochemical differences between organs and/or tissues, it is believed that MRI may be capable of differentiating different tissue types and in detecting diseases which induce physicochemical changes that may not be detected by x-ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment within which it finds itself.

In general, paramagnetic divalent or trivalent ions of elements with an atomic number of 21 to 29, 42 to 44 and 58 to 70 have been found effective as MRI image contrasting agents. Suitable such ions include chromium (III), manganese (II), manganese (III), iron (III), iron (II), cobalt (II), nickel (II), copper (II), praseodymium (III), neodymium (III), samarium (III) and ytterbium (III). Because of their very strong magnetic moments, gadolinium (III), terbium (III), dysprosium (III), holmium (III) and erbium (III) are preferred. Gadolinium (III) ions have been particularly preferred as MR image contrasting agents.

Typically, the divalent and trivalent paramagnetic ions have been administered in the form of complexes with organic complexing agents. Such complexes provide the paramagnetic ions in a soluble, non-toxic form, and facilitate their rapid clearance from the body following the imaging procedure. Gries et al., U.S. Pat. No. 4,647,447, disclose complexes of various paramagnetic ions with conventional aminocarboxylic acid complexing agents. A preferred complex disclosed by Gries et al. is the complex of gadolinium (III) with diethylenetriamine-pentaacetic acid ("DTPA"). This complex may be represented by the formula:

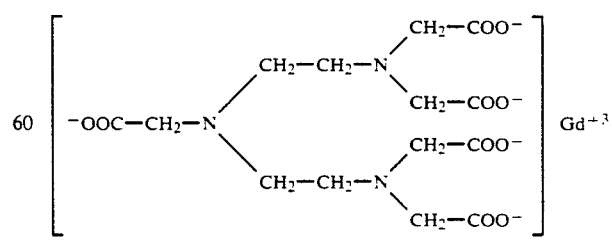

Paramagnetic ions, such as gadolinium (III), have been found to form strong complexes with DTPA. These complexes do not dissociate substantially in physiological aqueous fluids. The complexes have a net charge of −2, and generally are administered as soluble salts. Typical such salts are the sodium and N-methyl-glucamine salts.

The administration of ionizable salts is attended by certain disadvantages. These salts can raise the in vivo ion concentration and cause localized disturbances in osmolality, which in turn, can lead to edema and other undesirable reactions.

Efforts have been made to design non-ionic paramagnetic ion complexes. In general, this goal has been achieved by converting one or more of the free carboxylic acid groups of the complexing agent to neutral, non-ionizable groups. For example, S. C. Quay, in U.S. Pat. Nos. 4,687,658 and 4,687,659, discloses alkylester and alkylamide derivatives, respectively, of DTPA complexes. Similarly, published Dean, et al., U.S. Pat. No. 4,826,673 discloses mono- and polyhydroxyalkylamide derivatives of DTPA and their use as complexing agents for paramagnetic ions.

The nature of the derivative used to convert carboxylic acid groups to non-ionic groups can have a significant impact on tissue specificity. Hydrophilic complexes tend to concentrate in the interstitial fluids, whereas lipophilic complexes tend to associate with cells. Thus, differences in hydrophilicity can lead to different applications of the compounds. See, for example, Weinmann et al., *AJR*, 142, 679 (March, 1984) and Brasch et al., *AJR*, 142, 625 (March, 1984).

Thus, a need continues to exist for new and structurally diverse complexes of paramagnetic ions for use as MR imaging agents. There is further a need in the art to develop highly stable complexes with good relaxivity characteristics.

SUMMARY OF THE INVENTION

The present invention provides novel complexing agents and complexes of complexing agents with paramagnetic ions. The complexes are represented by the following formula 1:

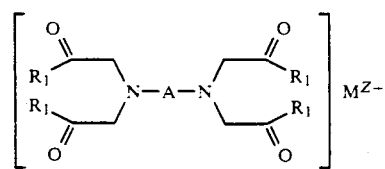

FORMULA 1 wherein A is —$CHR_2$—$CHR_3$ or —

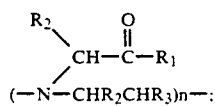

$M^{Z+}$ is a paramagnetic ion of an element with an atomic number 21–29, 42–44, or 58–70 and a valence, z, of 2+ or 3+; the $R_1$ groups may be the same or different selected from a group consisting of —O−,

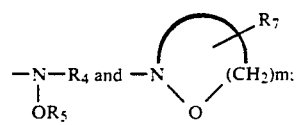

the $R_2$, $R_3$, $R_4$, $R_5$ and $R_7$ groups may be the same or different selected from a group consisting of hydrogen, alkyl -such as for example methyl or ethyl wherein methyl is preferable to reduce lipophilicity, acyl -such as for example acetyl, aryl -such as for example phenyl, benzoyl, mono- or poly- hydroxyalkyl -such as for example hydroxymethyl or dihydroxypropyl wherein dihydroxypropyl is preferable to enhance water solubility, mono- or polyalkoxyalkyl -such as for example methoxyethyl, aminoalkyl -such as for example aminomethyl, alkoxyaminoalkyl -such as for example methoxyaminomethyl, and acylaminoalkyl -such as for example acetylaminomethyl or proprionylaminomethyl; the carbon-containing R groups preferably contain 1 to 6 carbon atoms; n and m varies from preferably 1 to 6 and $R_2$ and $R_3$ may be joined together to form a 5, 6 or 7 membered ring.

Other complexes of the present invention are comprised by the following formula 2:

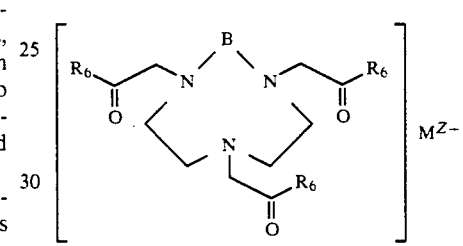

FORMULA 2 wherein B has the same definition as A in formula 1; $M^{Z+}$ has the same definition as $M^{Z+}$ in formula 1; the $R_6$ groups may be the same or different selected from the group consisting of —O−,

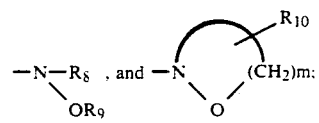

the $R_8$, $R_9$ and $R_{10}$ groups have the same definition as $R_2$, $R_3$, $R_4$, $R_5$ and $R_7$ of formula 1; the carbon-containing R groups preferably contain 1 to 6 carbon atoms; and m and n ranges preferably from 1 to 6.

Also disclosed is a diagnostic composition and a method of performing a MRI diagnostic procedure which involves administering to a warm-blooded animal an effective amount of the above-described complex and then exposing the warm-blooded animal to a MRI procedure, thereby imaging at least a portion of the body of the warm-blooded animal.

DETAILED DESCRIPTION OF THE INVENTION

The complexing agents employed in this invention are derivatives of well-known polyaminocarboxylic acid chelating agents, such as DOTA, DTPA, EDTA and cyclohexyldiaminotetraacetic acid. In these derivatives, some carboxylic acid groups of the polyaminocarboxylic acid are converted to N-alkoxyamide groups, such as those of the formula,

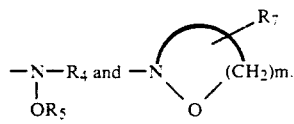

Thus, if the paramagnetic ion is trivalent and the chelating agent is DTPA, two of the carboxylic acid groups will be derivatized to the N-alkoxyamide form. Likewise, if the paramagnetic ion is divalent, three of the carboxylic acid groups of DTPA or two of the carboxylic acid groups of EDTA may be derivatized to the N-alkoxyamide form. When reacted with a divalent or trivalent paramagnetic ion, the resulting complexes could be substantially non-ionic as evidenced by very low electrical conductivity.

The N-alkoxyamide derivatives of the chelating agents are prepared in a conventional manner. In general, they are prepared by reacting a stoichiometric amount of an unsubstituted or substituted hydroxylamine compound of the formula,

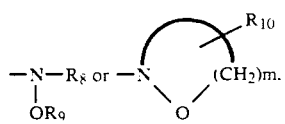

with a reactive derivative of the polyaminocarboxylic acid chelating agent under amide forming conditions. Such reactive derivatives include, for example, anhydrides, mixed anhydrides and acid chlorides. The ring can be saturated or unsaturated and substituted or unsubstituted. If the heterocyclic ring is substituted, the total number of substituents typically is 1 to 3.

In one embodiment, the reactions for preparing the N-alkoxyamide derivatives of the present invention are conducted in an organic solvent at an elevated temperature. Suitable solvents include those in which the reactants are sufficiently soluble and which are substantially unreactive with the reactants and products. Lower aliphatic alcohols, ketones, ethers, esters, chlorinated hydrocarbons, benzene, toluene, xylene, lower aliphatic hydrocarbons, and the like may advantageously be used as reaction solvents. Examples of such solvents are methanol, ethanol, n-propanol, isopropanol, butanol, pentanol, acetone, methylethyl ketone, diethylketone, methyl acetate, ethyl acetate, chloroform, methylene chloride, dichloroethane, hexane, heptane, octane, decane, and the like. If a DTPA or EDTA-type acid chloride is used as the starting material, then the reaction solvent advantageously is one which does not contain reactive functional groups, such as hydroxyl groups, as these solvents can react with the acid chlorides, thus producing unwanted by-products.

The reaction temperature may vary widely, depending upon the starting materials employed, the nature of the reaction solvent and other reaction conditions. Such reaction temperatures may range, for example, from about 20° C. to about 85° C., preferably from about 25° C. to about 50° C.

Following reaction of the reactive polyaminocarboxylic acid derivatives with the substituted hydroxylamine compound, any remaining anhydride or acid chloride groups can be hydrolyzed to the carboxylate groups by adding a stoichiometric excess of water to the reaction mixture and heating for a short time.

The resulting N-alkoxyamide is recovered from the reaction mixture by conventional procedures. For example, the product may be precipitated by adding a precipitating solvent to the reaction mixture, and recovered by filtration or centrifugation.

The paramagnetic ion is combined with the N-alkoxyamide derivative under complex-forming conditions. In general, any of the paramagnetic ions referred to above can be employed in making the complexes of this invention. The complexes can conveniently be prepared by mixing a suitable oxide or salt of the paramagnetic ion with the complexing agent in aqueous solution. To assure complete complex formation, a slight stoichiometric excess of the complexing agent may be used. In addition, an elevated temperature, e.g., ranging from about 20° C. to about 100° C., preferably from about 40° C. to about 80° C., may be employed to insure complete complex formation. Generally, complete complex formation will occur within a period from a few minutes to a few hours after mixing. The complex may be recovered by precipitation using a precipitating solvent such as acetone, and further purified by crystallization, if desired.

The novel complexes of this invention can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to 1.0M of a paramagnetic ion complex according to this invention. Preferred parenteral formulations have a concentration of paramagnetic ion complex of 0.1M to 0.5M. Such solutions also may contain pharmaceutically acceptable buffers and, optionally, electrolytes such as sodium chloride. The compositions may advantageously contain a slight excess, e.g., from about 0.001 to about 15 mole % excess, of a complexing agent associated with one or more physiologically acceptable, non-toxic cation. Such physiologically acceptable, non-toxic cations include sodium ions, calcium ions, magnesium ions, copper ions, zinc ions and the like and mixtures thereof. Calcium ions are preferred. A typical single dosage formulation for parenteral administration has the following composition:

Gadolinium DTPA-bis(N-alkoxyamide): 6.6 g
DTPA-bis(N-alkoxyamide): 260.0 mg
Calcium hydroxide: 37.0 mg
Distilled Water. 20.0 ml
pH: 7.2±0.2

Parenteral compositions may be injected directly or mixed with a large volume parenteral composition for systemic administration.

Formulations for enteral administration may vary widely, as is well-known in the art. In general, such formulations are liquids which include an effective amount of the paramagnetic ion complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the NMR image. Such doses may vary widely, depending upon the particular paramagnetic ion complex employed, the organs or tissues which are the subject of the imaging procedure, the NMR imaging equipment being used, etc. In general, parenteral dosages will range from about 0.001 to about 1.0 MMol of paramagnetic ion complex per kg of patient body weight. Preferred parenteral dosages range from about 0.005 to about 0.5 MMol of paramagnetic ion complex per kg of patient body weight. Enteral dosages generally range from about 0.5 to about 100 MMol, preferably from about 1.0 to about 20 MMol of paramagnetic ion complex per kg of patient body weight.

The novel MR image contrasting agents of this invention are expected to possess a unique combination of desirable features. The paramagnetic ion complexes should exhibit high solubility in physiological fluids, notwithstanding their substantially non-ionic character. This high solubility should allow the preparation of concentrated solutions, thus minimizing the amount of fluid required to be administered. The non-ionic character of the complexes also should reduce the osmolality of the diagnostic compositions, thus preventing undesired edema and other side effects.

The diagnostic compositions of this invention are used in the conventional manner. The compositions may be administered to a warm-blooded animal either systemically or locally to the organ or tissue to be imaged, and the animal then subjected to the MR imaging procedure. The compositions have been found to enhance the magnetic resonance images obtained by these procedures. In addition to their utility in magnetic resonance imaging procedures, the complexing agents of this invention may also be employed for delivery of radiopharmaceuticals and complexing heavy metals for x-ray contrast applications.

The invention is further illustrated by the following examples, which are not intended to be limiting.

EXAMPLE 1

Preparation of [N,N''-bis(N-methoxy-N-methyl)carbamoylmethyl]diethylenetriamine-N,N',N''-triacetic acid (2)

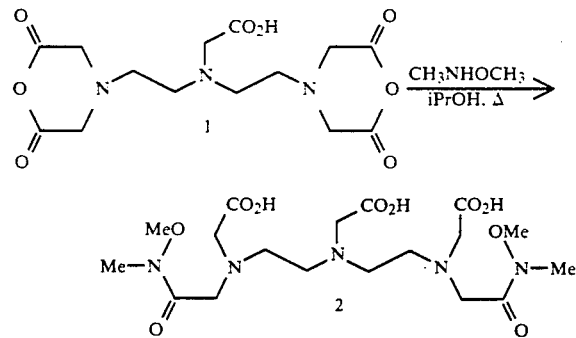

A stirred suspension of N,O-dimethyl(hydroxylamine hydrochloride (15.6 g, 0.16 mol) in anhydrous isopropyl alcohol (100 ml) was treated with 35 g of methanolic sodium methoxide (Aldrich, 25% w/w). The mixture was stirred at room temperature for 10 minutes and filtered to remove sodium chloride. The filtrate was added to a stirred suspension of DTPA-dianhydride (14.28 g, 0.04 mol) in anhydrous isopropyl alcohol (50 ml). The entire mixture was stirred at 50°-55° C. for six hours and thereafter at room temperature for 18 hours. The precipitate was collected by filtration, washed with isopropyl alcohol, dried, and recrystallized from n-propanol to give almost colorless solid. Anal. calcd. for $C_{18}H_{33}N_5O_{10}$: C,45.09; H,6.89; N,14.61. Found: C,45.00; H,7.28; N,14.59.

EXAMPLE 2

Preparation of [N,N''-bis(N-methoxy)carbamoylmethyl]diethylenetriamine-N,N',N''-triacetic acid (3)

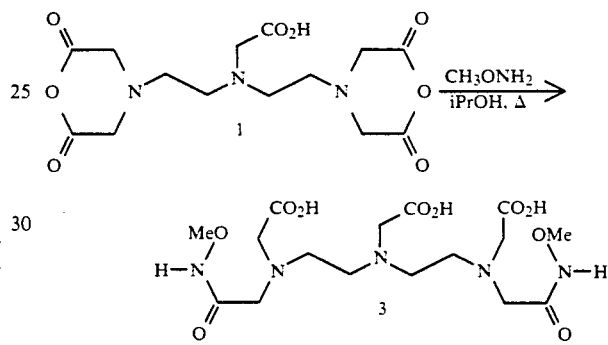

A stirred suspension of methoxylamine hydrochloride (13.36 g, 0.16 mol) in anhydrous isopropyl alcohol (100 ml) was treated with 35 of methanolic sodium methoxide (Aldrich, 25% w/w). The mixture was stirred at room temperature for 10 minutes and filtered to remove sodium chloride. The filtrate was added to a suspension of DTPA-dianhydride (14.28 g, 0.04 mol) in anhydrous isopropyl alcohol (50 ml). The entire mixture was stirred at 50°-55° C. for two hours. The gummy suspension was treated with methanol (150 ml) and filtered to remove undissolved impurities. Evaporation of the solvent under reduced pressure afforded colorless solid which was recrystallized from methanol/isopropanol/water to give colorless solid (6.2 g, 40%). $^{13}$C-NMR (D$_2$O) δ(ppm): 175.3, 171.4, 168.9, 65.1, 56.9, 56.4, 56.0, 53.6, 51.0.

EXAMPLE 3

Preparation of {N,N''-bis[N-(2-hydroxy)ethoxy]carbamoylmethyl}diethylenetriamine-N,N',N''-triacetic acid (4b)

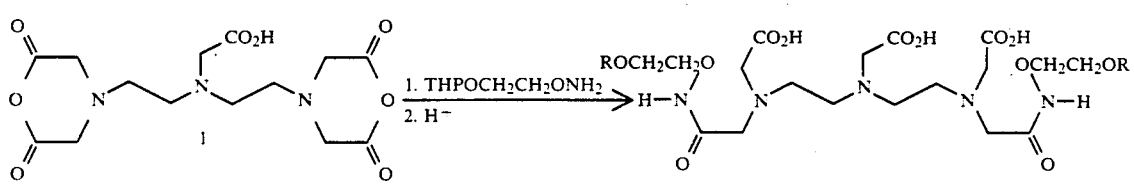

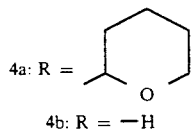

4a: R = (tetrahydropyranyl ether)
4b: R = —H

To a slurry of the dianhydride of diethylenetriamine pentaacetic acid, 1, (7.6 g, 0.021 mole) in 105 mL of isopropanol was added a solution of the tetrahydropyanyl ether of (2-hydroxyethoxy)amine, (6.9 g, 0.043 mole) in 10 mL of isopropanol. The mixture was then heated to 60° C. under nitrogen atmosphere for 20 hours. After the reaction mixture was cooled to 25° C., the solvent was decanted from the resulting semisolid which had precipitated. Trituration of this residue with hexane gave a tan powder which was further purified via silica gel chromatography using a methanol/dichloromethane gradient. The purest fractions were combined and characterized by $^1$H and $^{13}$C NMR to be the desired bisamide 4a. The tetrahydropyranyl blocking groups were removed by stirring 4a with 75 ml of 10% hydrochloric acid at 25° for 20 hours. The pH of the reaction mixture was adjusted to 7 with solid sodium bicarbonate and the solvents were stripped to dryness under reduced vacuum. The solids were triturated with methanol and the combined extracts were evaporated to give a yellow oil. This serum was purified over reversed phase packing using a water/methanol gradient to give 4b.

EXAMPLE 4

Preparation of
{N,N''-bis[N-methoxy-N-methyl)carbamoylmethyl]-
diethylenetriamine-N,N',N''-triaceto}gadolinium(III)
(5)

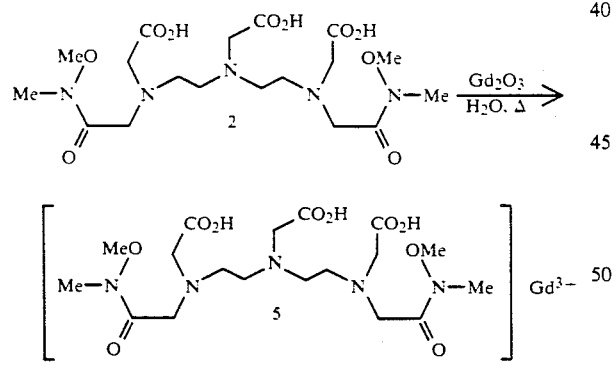

A mixture of the ligand 2 (15.1 g, 0.034 mol) and gadolinium oxide (5.34 g, 0.015 mol) in deionized distilled water (50 ml) was heated at 65°-70° C. for 24 hours. The solution was filtered through a fine porosity sintered glass funnel to remove undissolved impurities and the filtrate was poured onto acetone (2L). After stirring the mixture for about 1 hour, the solid was collected, washed with acetone, dried, and recrystallized from methanol/dimethoxyethane to give colorless solid (14.5 g, 80%). Anal. calcd. for $C_{18}H_{30}O_{10}Gd \times 1.6$ $H_2O$: C,32.63; H,5.02; N,10.57; Gd,23.72; $H_2O$,4.38. Found: C,32.67; H,5.11; N,10.20; Gd,23.45; $H_2O$,4.21.

I claim:

1. A complex comprising the following formula:

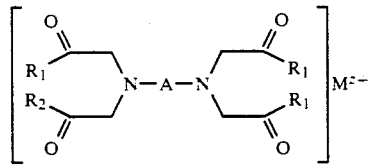

wherein $M^{z+}$ is a paramagnetic ion of an element with an atomic number 21-29, 42-44, or 58-70 and a valence, z, of 2+ or 3+; A is selected from the group consisting of

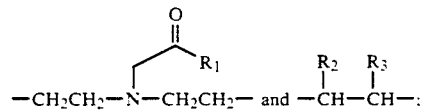

the $R^1$ groups are selected from a group consisting of —O$^-$ and

wherein at least one $R_1$ group is

the $R_2$, $R_3$, $R_4$, and $R_5$ groups may be the same or different selected from a group consisting of alkyl, acyl, aryl, mono- or polyhydroxyalkyl, mono- or poly-alkoxyalkyl, aminoalkyl and acylaminoalkyl; the carbon-containing R groups preferably contain 1 to 6 carbon atoms; where $R_2$ and $R_3$ may be joined together to form a 5, 6 or 7 membered ring.

2. The complex of claim 1, wherein A is

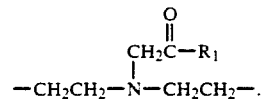

3. The complex of claim 2, wherein $M^{z+}$ is selected from a group consisting of praseodymium (III), neodymium (III), sumarium (III), ytterbium (III), gadolinium (III), terbium (III), dysprosium (III), holmium (III) erbium (III), iron (III), and manganese (II).

4. The complex of claim 2, wherein $R_4$ and $R_5$ are both methyl and $M^{z+}$ is $Gd^{3+}$, $Dy^{3+}$ or $Fe^{3+}$.

5. The complex of claim 2, wherein $R_5$ is methyl and $M^{z+}$ is $Gd^{3+}$, $Dy^{3+}$ or $Fe^{3+}$.

6. The complex of claim 2, wherein $R_5$ is hydroxyethyl and $M^{z+}$ is $Gd^{3+}$, $Dy^{3+}$ or $Fe^{3+}$.

7. The complex of claim 1, wherein A is —CHR$_2$CHR$_3$— and $R_2$ and $R_3$ are selected from a group consisting of hydrogen and alkyl, which may join together to form a 5, 6 or 7 membered ring.

8. The complex of claim 7, wherein $M^{Z+}$ is selected from a group consisting of praseodymium (III), neodymium (III), samarium (III), ytterbium (III), gadolinium (III), terbium (III), dysprosium (III), holmium (III) erbium (III), iron (III) and manganese (II).

9. The complex of claim 7, wherein $R_4$ and $R_5$ are both methyl and $M^{Z+}$ is $Mn^{2+}$.

10. The complex of claim 7, wherein $R_5$ is methyl and $M^{Z+}$ is $Gd^{3+}$, $Dy^{3+}$ or $Fe^{3+}$.

11. The complex of claim 7, wherein $R_5$ is hydroxyethyl and $M^{Z+}$ is $Gd^{3+}$, $Dy^{3+}$ or $Fe^{3+}$.

12. A diagnostic composition suitable for enteral or parenteral administration to a warm-blooded animal, which comprises a MRI-effective amount of a complex of a paramagnetic ion comprising the following formula:

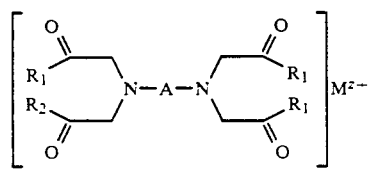

wherein $M^{Z+}$ is a paramagnetic ion of an element with an atomic number 21-29, 42-44, or 58-70 and a valence, z, of 2+ or 3+; A is selected from the group consisting of

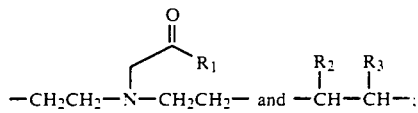

the $R^1$ groups are selected from a group consisting of —O— and

wherein at least one $R_1$ group is

the $R_2$, $R_3$, $R_4$, and $R_5$ groups may be the same or different selected from a group consisting of alkyl, acyl, aryl, mono- or polyhydroxyalkyl, mono- or poly-alkoxyalkyl, aminoalkyl and acylaminoalkyl; the carbon-containing R groups preferably contain 1 to 6 carbon atoms; where $R_2$ and $R_3$ may be joined together to form a 5, 6 or 7 membered ring; and a pharmaceutically acceptable carrier.

13. The composition of claim 12, wherein A is

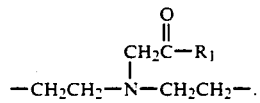

14. The composition of claim 13, wherein $M^{Z+}$ is selected from a group consisting of praseodymium (III), neodymium (III), samarium (III), ytterbium (III), gadolinium (III), terbium (III), dysprosium (III), holmium (III), erbium (III), iron (III) and manganese (II).

15. The composition of claim 13, wherein $R_4$ and $R_5$ are both methyl and $M^{Z+}$ is $Gd^{3+}$, $Dy^{3+}$ or $Fe^{3+}$.

16. The composition of claim 13, wherein $R_5$ is methyl and $M^{Z+}$ is $Gd^{3+}$, $Dy^{3+}$ or $Fe^{3+}$.

17. The composition of claim 13, wherein $R_5$ is hydroxyethyl and $M^{Z+}$ is $Gd^{3+}$, $Dy^{3+}$ or $Fe^{3+}$.

18. The composition of claim 12, wherein the composition contains a pharmaceutically acceptable buffer and a pharmaceutically acceptable electrolyte.

19. The composition of claim 12, wherein the composition contains an excess of a complexing agent.

20. The composition of claim 12, wherein the composition contains an excess complexing agent preferably employed in an amount ranging from 0.01 to 15 mole % excess, relative to the paramagnetic metal complex, and is complexed with a cation selected from a group consisting of sodium ions, calcium ions, magnesium ions, copper ions and zinc ions and mixtures thereof.

21. The composition of claim 12, wherein the composition contains an excess complexing agent complexed with calcium ions.

22. The composition of claim 12, wherein the composition contains an excess complexing agent complexed with one or more physiologically acceptable, non-toxic cations.

23. The composition of claim 12, wherein A is —CHR$_2$CHR$_3$—, and R$_2$ and R$_3$ are selected from a group consisting of hydrogen and alkyl, which may join together to form a 5, 6 or 7 membered ring.

24. The composition of claim 23, wherein $R_4$ is methyl; $R_5$ is either methyl or hydroxyethyl; and $M^{Z+}$ is $Mn^{2+}$.

25. A method of performing a MRI diagnostic procedure, which comprises:
(a) administering to a warm-blooded animal a diagnostically effective amount of a complex of the formula:

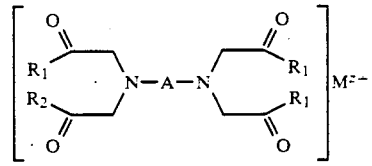

wherein $M^{Z+}$ is a paramagnetic ion of an element with an atomic number 21-29, 42-44, or 58-70 and a valence, z, of 2+ or 3+; A is selected from the group consisting of

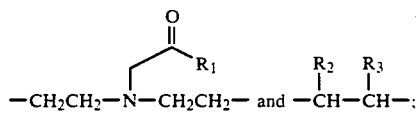

the $R^1$ groups are selected from a group consisting of —O— and

wherein at least one $R_1$ group is

the $R_2$, $R_3$, $R_4$, and $R_5$ groups may be the same or different selected from a group consisting of alkyl, acyl, aryl, mono-or poly-hydroxyalkyl, mono- or poly-alkoxyalkyl, aminoalkyl and acylaminoalkyl; the carbon-containing R groups preferably contain 1 to 6 carbon atoms; where $R_2$ and $R_3$ may be joined together to form a 5, 6 or 7 membered ring; and (b) exposing the animal to a MRI procedure, thereby imaging at least a portion of the body of the warm-blooded animal.

26. A method of performing a MRI diagnostic procedure as defined in claim 25, wherein A is

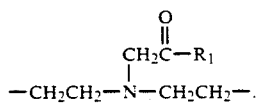

27. A method of performing a MRI diagnostic procedure as defined in claim 25, wherein $M^{Z+}$ is selected from a group consisting of praseodymium(III), neodymium(III), samarium(III), ytterbium(III), gadolinium(III), terbium(III), dysprosium(III), holmium(III), erbium(III), iron(III), and manganese(II).

28. A method of performing a MRI diagnostic procedure as defined in claim 25, wherein $R_4$ is methyl, $R_5$ is either methyl or hydroxyethyl, and $M^{Z+}$ is $Gd^{3+}$, $Dy^{3+}$, or $Fe^{3+}$.

29. A method of performing a MRI diagnostic procedure as defined in claim 25, wherein the complex is combined with a pharmaceutically acceptable buffer.

30. A method of performing a MRI diagnostic procedure as defined in claim 25, wherein the complex is combined with a pharmaceutically acceptable buffer and a pharmaceutically acceptable electrolyte.

31. A method of performing a MRI diagnostic procedure as defined in claim 25, wherein the complex is combined with an excess of a complexing agent, said complexing agent being optionally complexed with one or more physiologically acceptable nontoxic cations.

32. A method of performing a MRI diagnostic procedure of as defined in claim 25, wherein the complex is combined with an excess complexing agent employed in an amount ranging from 0.01 to 15 mole percent excess, relative to the paramagnetic metal complex, said excess complexing agent being complexed with a cation selected from a group consisting of sodium, calcium, magnesium, copper, and zinc ions, and mixtures thereof.

33. A method of performing a MRI diagnostic procedure of as defined in claim 25, wherein the complex is combined with an excess complexing agent complexed with calcium ions.

34. A method of performing a MRI diagnostic procedure of as defined in claim 25, wherein A is $-CHR_2CHR_3-$, and $R_2$ and $R_3$ are selected from a group consisting of hydrogen and alkyl, which may join to form a 5, 6 or 7 membered ring.

* * * * *